(12) United States Patent
Keppler et al.

(10) Patent No.: US 9,339,281 B2
(45) Date of Patent: May 17, 2016

(54) SURGICAL GUIDING TOOLS AND SYSTEMS AND METHODS OF MANUFACTURING SURGICAL GUIDING TOOLS

(71) Applicant: Materialise NV, Leuven (BE)

(72) Inventors: Louis Keppler, Leuven (BE); Nele Daeman, Bonheiden (BE); Katerina Nikonenko, Leuven (BE)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 14/628,528

(22) Filed: Feb. 23, 2015

(65) Prior Publication Data

US 2015/0157343 A1    Jun. 11, 2015

Related U.S. Application Data

(63) Continuation of application No. 14/010,256, filed on Aug. 26, 2013, now abandoned.

(60) Provisional application No. 61/693,525, filed on Aug. 27, 2012.

(51) Int. Cl.
| | |
|---|---|
| *A61B 17/58* | (2006.01) |
| *A61B 17/17* | (2006.01) |
| *A61B 17/56* | (2006.01) |
| *A61B 17/00* | (2006.01) |

(52) U.S. Cl.
CPC .............. *A61B 17/1764* (2013.01); *A61B 17/56* (2013.01); *A61B 2017/00862* (2013.01); *A61B 2017/568* (2013.01)

(58) Field of Classification Search
CPC .......................... A61B 17/155; A61B 17/1764

USPC .................................................. 606/86 R–89
See application file for complete search history.

(56) References Cited

U.S. PATENT DOCUMENTS

| | | | |
|---|---|---|---|
| 2010/0286700 A1* | 11/2010 | Snider et al. | 606/89 |
| 2011/0015637 A1 | 1/2011 | De Smedt | |
| 2011/0015639 A1 | 1/2011 | Metzger et al. | |
| 2012/0277751 A1* | 11/2012 | Catanzarite et al. | 606/88 |
| 2013/0053854 A1* | 2/2013 | Schoenefeld et al. | 606/87 |

FOREIGN PATENT DOCUMENTS

| | | |
|---|---|---|
| EP | 2529677 A1 | 12/2012 |
| WO | 2011110374 A1 | 9/2011 |

OTHER PUBLICATIONS

International Search Report issued Nov. 6, 2013 on related Application No. PCT/EP2013/067721 filed Aug. 27, 2013.

* cited by examiner

*Primary Examiner* — Matthew Lawson
(74) *Attorney, Agent, or Firm* — Fairview IP

(57) ABSTRACT

The present application relates to surgical guiding tools that may be used for guiding a surgical instrument during bone surgery. A surgical guiding tool may include a body including one or more clamps configured to attach the surgical guiding tool to one or more portions of the bone, wherein a first clamp of the one or more clamps includes a snap-fit portion including a flexible structure for increasing a clamping force of the first clamp and allowing ease of removal of the surgical guiding tool from the bone. The surgical guiding tool may further include at least one aperture for guiding a surgical instrument. The present application further provides methods for manufacturing surgical guiding tools and uses of the tools for placement onto a bone.

18 Claims, 8 Drawing Sheets

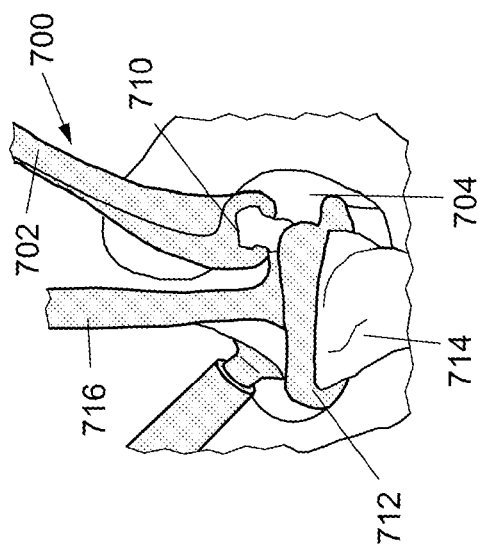
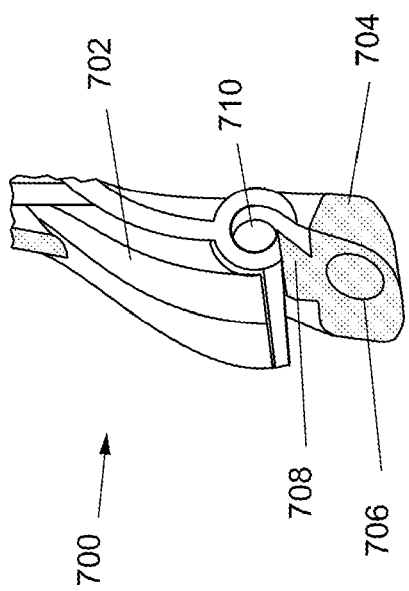
FIG. 7b
FIG. 7a

SURGICAL GUIDING TOOLS AND SYSTEMS AND METHODS OF MANUFACTURING SURGICAL GUIDING TOOLS

CROSS-REFERENCE TO RELATED APPLICATIONS

This application is a continuation of U.S. patent application Ser. No. 14/010,256, filed Aug. 26, 2013, which claims the benefit of U.S. Provisional Application No. 61/693,525, filed Aug. 27, 2012, the entire disclosure of each of which is hereby incorporated by reference.

BACKGROUND OF THE INVENTION

1. Field of the Invention

The present application relates to surgical guiding tools for use in guiding a surgical instrument during orthopedic surgery. This application also relates to methods for manufacturing surgical guiding tools and methods for using the surgical guiding tools in bone surgery.

2. Description of the Related Technology

Surgical guiding tools assist surgeons and have wide applications in orthopedic surgery. Surgical guiding tools may allow a surgeon to accurately transfer a preoperative surgical plan into the operating room. Further, surgical guiding tools may help guide a surgical instrument, such as a cutting or drilling instrument, along a pre-defined cutting or drilling path.

Problems may arise when adjustable surgical guiding tools, which may include components that can be positioned to attach to or around a part of the bone, are unstable or provide inaccurate surgical instrument guiding positions. For example, a surgical guiding tool may not fit well on a patient's bone and may be unstable as a result. Furthermore, the guiding position for a surgical instrument may be imprecise because of the amount of distance between the supporting anatomy and the planned point of entry of the surgical instrument. Still further, surgical guiding tools may be large or bulky, and may require the availability of a large surgical window.

In light of these and other deficiencies recognized by the inventors, there is a need for surgical guiding tools that provide secure and stable attachment to a patient's bone and that provide the ability to accurately and efficiently guide a surgical instrument into or onto the patient's bone.

SUMMARY

Various implementations of systems, methods and devices within the scope of the appended claims each have several aspects, no single one of which is solely responsible for the desirable attributes described herein. Without limiting the scope of the appended claims, some prominent features are described herein.

The present application relates generally to surgical guiding tools that may be patient-specific. Details of one or more implementations of the subject matter described in this specification are set forth in the accompanying drawings and the description below. Other features, aspects, and advantages will become apparent from the description, the drawings, and the claims.

One aspect of the subject matter described in the disclosure provides a surgical guiding tool for a bone. The surgical guiding tool includes a body including one or more clamps configured to attach the surgical guiding tool to one or more portions of the bone, wherein a first clamp of the one or more clamps includes a snap-fit portion including a flexible structure for increasing a clamping force of the first clamp and allowing ease of removal of the surgical guiding tool from the bone. The body further includes at least one aperture for guiding a surgical instrument.

Another aspect of the subject matter described in the disclosure provides a method of manufacturing a surgical guiding tool. The method includes designing the surgical guiding tool to create a surgical guiding tool design, wherein the surgical tool design includes a body including one or more clamps configured to attach the surgical guiding tool to one or more portions of a bone, wherein a first clamp of the one or more clamps includes a snap-fit portion including a flexible structure for increasing a clamping force of the first clamp and allowing ease of removal of the surgical guiding tool from the bone. The body further includes at least one aperture for guiding a surgical instrument. Furthermore, the method includes manufacturing the surgical guiding tool based on the surgical guiding tool design.

Yet another aspect of the subject matter described in the disclosure provides a femoral surgical guiding tool for a distal end of a femur. The femoral surgical guiding tool includes a body including an anterior portion configured to attach the surgical guiding tool to one or more osteophytes on an anterior region of the femur. The body further includes one or more clamps configured to attach the surgical guiding tool to one or more condyles of the femur and at least one aperture for guiding a surgical instrument.

BRIEF DESCRIPTION OF THE DRAWINGS

The following description of the figures is merely exemplary in nature and is not intended to limit the present teachings, their application or uses. Throughout the drawings, corresponding reference numerals indicate like or corresponding parts and features. Note that the relative dimensions of the following figures may not be drawn to scale.

FIGS. 7a and 7b illustrates an example of a clamping structure that may act as a retractor.

DETAILED DESCRIPTION OF CERTAIN INVENTIVE EMBODIMENTS

Figure 1A:
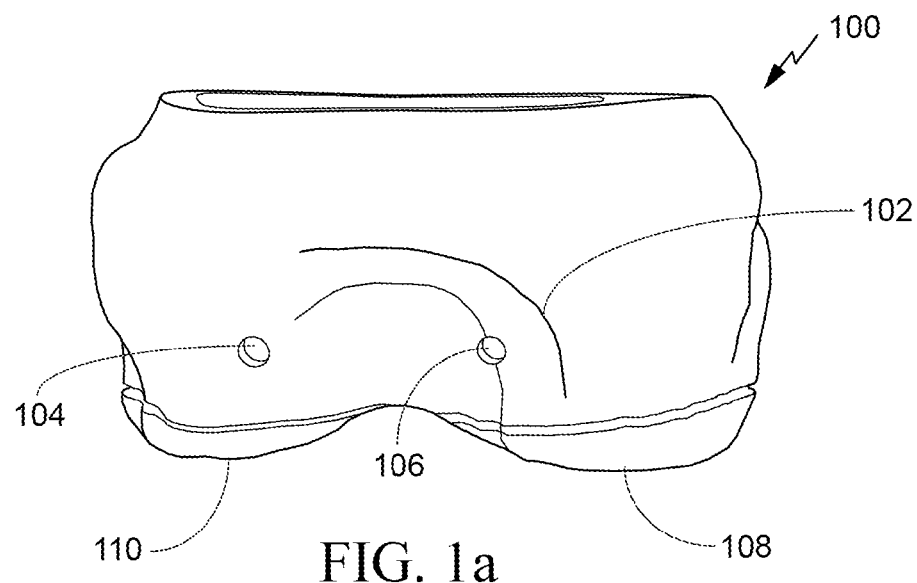
FIG. 1a illustrates an example of an anterior view of a femur.

The following detailed description is directed to certain specific embodiments. However, the teachings herein can be applied in a multitude of different ways. In this description, reference is made to the drawings wherein like parts are designated with like numerals throughout.

The present application will be described with respect to particular embodiments but the invention is not limited thereto but only by the claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Reference throughout this specification to "one embodiment" or "an embodiment" means that a particular feature, structure or characteristic described in connection with the embodiment is included in at least one embodiment of the present application. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the application, and form different embodiments, as would be understood by those in the art. For example, in the appended claims, any of the features of the claimed embodiments can be used in any combination.

The term "about" as used herein when referring to a measurable value such as a parameter, an amount, a temporal duration, and the like, is meant to encompass variations of +/−10% or less, preferably +/−5% or less, more preferably +1/−1% or less, and still more preferably +1/−0.1% or less of and from the specified value, insofar as such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present application discloses surgical guiding tools that may be patient-specific. The surgical guiding tools provide accurate and stable attachment to a bone, which allows stable and accurate introduction of a surgical instrument into the bone. This application further describes medical-image-based surgical guiding tools that may be patient specific. These patient-specific tools may provide the ability to accurately insert a surgical instrument into the patient's bone according to a predefined planning.

The term "patient-specific" as used herein refers to the surgical devices, tools, and/or guides as described herein, which are designed starting from an individual patient's anatomy to provide patient-specific devices, tools, or guides having a custom fit or functioning in a unique, customized manner for a particular individual patient. The use of patient-specific devices, tools, or guides allows for improved or optimized surgical interventions, orthopedic structures, and/or kinematics for the patient. Similar benefits are obtained when such patient-specific devices are used in combination with standard implants, tools, devices, surgical procedures, and/or other methods.

In some embodiments, a surgeon or physician during pre-operative procedures may identify various regions of a bone of a specific patient, such as those described below with respect to the femur 100, and may determine, based on the identified regions of the bone, an optimal design for various surgical guiding tool components (e.g., a clamp, body, aperture, etc. of a surgical guiding tool). A surgeon or physician may further determine optimal locations for attaching a surgical guiding tool based on the identified regions of the bone. Pre-operative procedures often involve obtaining an image of a patient's bone prior to performing surgery. Digital patient-specific image information may be provided by any suitable means known in the art, such as, for example, a computer tomography (CT) scanner, a magnetic resonance imaging (MRI) scanner, an x-ray, or an ultrasound scanner.

An advantage of the surgical guiding tools described in the present application provides that sufficient information may be obtained for designing a guiding tool for secure and stable placement onto a patient's bone based on either CT or MRI images. Cartilage regions of bones may not be visible on the images of CT scans, and, as a result, these cartilage regions may not be used to fit a surgical guiding tool on the patient. A physician may be unable to locate an optimal position or region on the bone for attachment of the surgical guiding tool due to the limited regions of the bone that are visible to the physician. Thus, available attachment regions on the bones for guiding tools may be limited. Accordingly, surgical guiding tools that are able to provide a secure and stable attachment to the bone, along with methods for identifying optimal locations on the bone, even with limited attachment regions are desirable.

Pre-operative planning may include the construction of a three dimensional (3D) virtual model of a bone, or part thereof. In some embodiments, construction of the 3D virtual model may begin with scanning of a patient. For example, the scanning may include using a scanning technique that generates medical volumetric data, such as a CT scan, a MRI scan, or the like. In some embodiments, the output of the scan may include a stack of two-dimensional (2D) slices forming a 3D data set. The output of the scan may be digitally imported into a computer program and may be converted using algorithms known in the field of image processing technology to produce a 3D computer model of the bone. For example, the virtual 3D model may be constructed from the data set using a computer program such as Mimics™ as supplied by Materialise N.V., Leuven, Belgium. Once the 3D volume of the bone, or a part thereof, is reconstructed, the surgeon may define the preferred position, orientation, depth and diameter of the bores and drill paths that are needed for the surgery. Based on the determined surgical needs, the surgeon or a physician may design, manufacture, and/or manipulate a surgical guiding tool to meet the needs of the specific patient.

FIG. 1a illustrates one example of an anterior view of a femur 100. While the description herein describes a femur, one of skill in the art will understand that the content of the present application applies equally to other bones, such as the humerus, scapula, tibia, fibula, talus, and other shoulder, hip, ankle, and/or finger bones. The anterior region depicted in FIG. 1a is located at the distal end of the femur 100. This anterior region of the femur 100 may provide a portion 102 that may be used to attach and secure a surgical guiding tool thereto. For example, osteophytes may be located on the anterior region of the femur 100, and may be used to attach a surgical guiding tool to the femur 100. An osteophyte is a bony projection that forms along bones, such as at a joint, and may occur in patients with arthritis. One or more osteophytes projecting from the surface of a femur, for example, may provide a surface from which a surgical guiding tool may be attached (e.g., in whole or in part). A medial condyle 108 and a lateral condyle 110 are also located at the distal end of the femur 100. Holes 104 and 106 may be aligned with one or more apertures of a surgical guiding tool and may be created using a surgical tool device (e.g., a surgical drill) inserted into the one or more apertures. Details regarding various embodiments of surgical guiding tools will be discussed below.

Figure 1B:
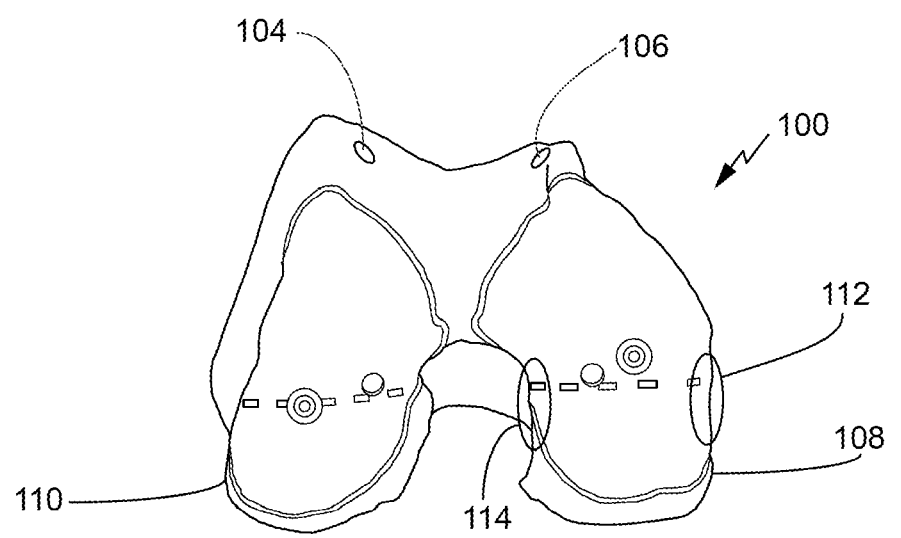
FIG. 1b illustrates examples of alternative views of a femur.

FIG. 1b illustrates examples of alternative views of the femur 100 illustrated in FIG. 1a. In particular, FIG. 1b illustrates the medial condyle 108 and the lateral condyle 110 located at the distal end of the femur 100. The medial 108 and lateral 110 condyles may also provide one or more portions that may be used to attach and secure a surgical guiding tool thereto. For example, a lateral region 112 and a medial region 114 of the medial condyle 108 may be used to attach and secure a surgical guiding tool. In some embodiments, lateral and medial regions of the lateral condyle 110 may be used to attach and secure a surgical guiding tool. For example, lateral and medial regions of the lateral condyle 110 may be used in addition to the lateral region 112 and medial region 114 of the medial condyle 108 to attach a surgical guiding tool to the femur 100. As another example, only the lateral and medial regions of the lateral condyle 110 may be used as an alternative to the lateral region 112 and medial region 114 of the medial condyle 108. In some embodiments, osteophytes located on the medial condyle 108 and/or the lateral condyle 110 may be used to attach and secure a surgical guiding tool.

In some embodiments, as indicated above, the patient-specific regions of a bone may comprise specific anatomical features that may be used to attach a surgical guiding tool. Detailed geometrical, patient-specific information is used in the design and manufacture of a surgical guiding tool in order to determine those surfaces of the bone that are suitable for this purpose. For example, as described above, one or more osteophytes projecting from the surface of a bone, such as a femur, may provide a surface from which a surgical guiding tool may be attached. In addition to the osteophytes, a medial condyle 108 and/or a lateral condyle 110 may provide one or more portions that may be used to attach and secure a surgical guiding tool thereto. In some embodiments, the medial condyle 108 and/or the lateral condyle 110 may be used to attach a surgical guiding tool to the bone independently of the one or more osteophytes.

A method of manufacturing a surgical guiding tool may include designing the surgical guiding tool to create a surgical tool design, which may include identifying and selecting at least one part of a bone that contains specific features that may allow attachment of the surgical guiding tool. For example, a surgical guiding tool for a bone may be designed and manufactured, and may comprise a body including one or more clamps. The clamps may take various forms and perform various functions including, but not limited to, attaching and/or securing the guiding tool to a bone. In some embodiments, the clamps are configured to attach the surgical guiding tool to one or more portions of the bone, wherein a first clamp of the one or more clamps includes a snap-fit portion including a flexible structure for increasing a clamping force of the first clamp and allowing ease of removal of the surgical guiding tool from the bone. The flexible structure may include any structure that can be used to increase the clamping force of the first clamp and to ease removal of the surgical guiding tool from the bone. For example, as discussed further below, the flexible structure may include a snap-fit portion with a material having a thickness that is less than the average thickness of the remainder of the body. As another example, the flexible structure may include one or more attachment mechanisms, such as a group of bands or chains or a honeycomb structure, that interconnect a first portion (e.g., a medial portion) of the first clamp to a second portion (e.g., lateral) of the first clamp. Further examples of a flexible structure may include attachment mechanisms using one or more screws to lock an undercut portion in place, using a retractor, using a spring loaded lock, using a spring combined with a hinge, using a push button locking mechanism, etc. The flexible structure may further include a reference mechanism that can be used to confirm that the surgical guiding tool is properly attached to the bone. The surgical guiding tool (e.g., the body) may further comprise at least one aperture for guiding a surgical instrument. In another example, a femoral surgical guiding tool for a distal end of a femur may be designed and manufactured, and may comprise a body including an anterior portion configured to attach the surgical guiding tool to one or more osteophytes on an anterior region of the femur, and one or more clamps configured to attach the surgical guiding tool to one or more condyles of the femur. In this example, the femoral surgical guiding tool (e.g., the body) may further comprise at least one aperture for guiding a surgical instrument.

Manufacturing and/or designing of a surgical guiding tool may further include determining the appropriate position of a guiding component of the surgical guiding tool (e.g., an aperture) with regard to the bone. In particular embodiments, this may be done based on the pre-operative planning of the desired path of the surgical tool in the bone. The orientation of the guiding component may be such that the surgical instrument is guided in the predetermined direction. Pre-operative planning by a physician makes it possible to determine the required path of the surgical instrument, and accordingly, the required orientation of the guiding component. The pre-operative planning may be done using suitable dedicated software, based on suitable medical images (of which CT, MRI, are examples), taking into account factors like bone quality and proximity to nerve bundles/blood vessels, or other anatomically sensitive objects. In some embodiments, preoperative images are imported into a computer workstation running 3D software in order to plan and simulate the surgery. The imported images may be manipulated as 3D volumes, and a computer simulation may be created, which outputs a planning containing the information necessary for adapting the orientation of the guiding component.

Manufacturing of a surgical guiding tool may further comprise manufacturing the surgical guiding tool based on the design. FIG. 7 provides an example of a method of manufacturing a surgical guiding tool, and is described in further detail below.

Figures 2A, 2B:
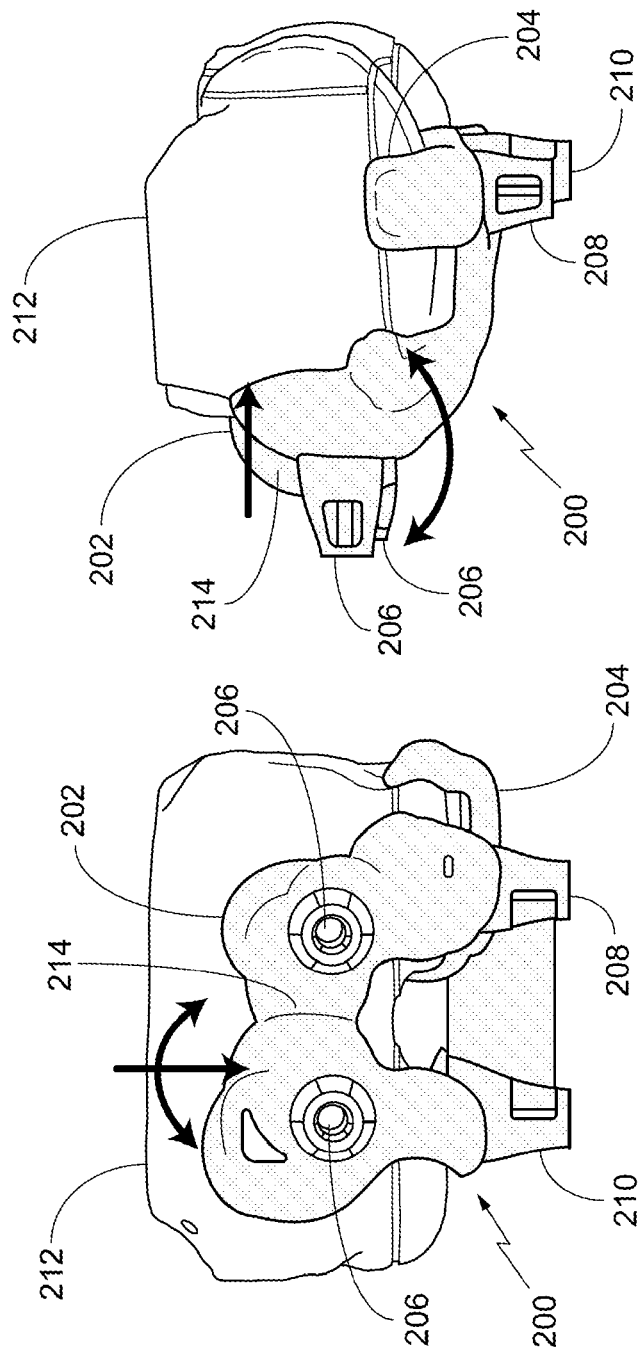
FIGS. 2a and 2b illustrate an example of a surgical guiding tool configured to attach to a bone.

FIGS. 2a and 2b illustrate an example of a surgical guiding tool 200 configured to attach to a bone. In some embodiments, the surgical guiding tool 200 may be a femoral surgical guiding tool for a distal end of a femur 212. While the description herein may describe a femur 212 as an example of the bone, one of skill in the art will understand that the content of the present application applies equally to other bones, such as the humerus, scapula, tibia, fibula, talus, spine, and other shoulder, hip, ankle, and/or finger bones. The surgical guiding tool 200 includes a body 202 that is configured to attach to at least one region or portion of the femur 212. The body 202 includes a first portion 214, such as an anterior portion, that is configured to attach the surgical guiding tool to an anterior region of the femur 212. For example, the first portion 214 may be configured to attach the surgical guiding tool 200 to one or more osteophytes on the anterior region of a femur 212. In some embodiments, the first portion 214 may be configured to attach the surgical guiding tool to one or more osteophytes anywhere along a bone, such as one or more osteophytes on the distal end of a humerus. The first portion 214 attaches and secures the surgical guiding tool 200 to the femur 212. For example, the first portion 214 may be configured to rest on one or more osteophytes and thus restrict undesired movement of the surgical guiding tool 200. In this example, as further described below, a clamp 204 may be used to secure the surgical guiding tool 200 to the femur 212. In some embodiments, the first portion 214 may include a flexible snap-fit portion for increasing a clamping force of the first portion 214 to the femur 212 and allowing ease of removal of the surgical guiding tool 200 from the femur 212. For example, the first portion 214 may be manufactured from a flexible material that creates a clamping force for squeezing a portion of a femur 212 (e.g., an osteophyte), and at the same time allows a physician to easily remove the surgical guiding tool 200 from the femur 212.

The body 202 of the surgical guiding tool 200 further includes a clamp 204 configured to attach the surgical guiding tool 200 to one or more portions of the femur 212. For example, the clamp 204 may be configured to attach the surgical guiding tool 200 to a condyle of the femur 212, such as the medial condyle as illustrated in FIGS. 2*a* and 2*b*. The secure attachment of the clamp 204 to a condyle ensures that the surgical guiding tool 200 remains in a stable and secure position during surgery. The extent of displacement of the clamp 204 that is needed to place the surgical guiding tool 200 onto the femur 212 depends on the thickness of the portion of the femur 212 (e.g., a condyle) that the clamp is to be attached and the extent to or the angle by which the clamp 204 spans the contour of the portion of the femur 212 upon placement of the surgical guiding tool thereon. In some embodiments, an overhang of the ends (referred to as an "undercut" portion) of the clamp 204 is created when the surgical guiding tool 200 is placed on the femur 212. For example, the undercut portion of the clamp 204 may form a clamping or snapping mechanism that encloses the condyle and creates a stable and secure attachment of the surgical guiding tool 200 to the femur 212. In some embodiments, the clamp 204 may include a snap-fit portion including a flexible structure for increasing a clamping force of the clamp 204 and allowing ease of removal of the surgical guiding tool 200 from the femur 212. For example, a snap-fit portion of the clamp 204 including the flexible structure may be configured to allow a stable and secure attachment of the surgical guiding tool 200 to a condyle of the femur 212 by increasing the clamping force of the clamp 204, while allowing a physician to remove the surgical guiding tool 200 from the femur 212 with ease. Details regarding different embodiments of a snap-it portion of a clamp are described below. In some embodiments, the body 202 of the surgical guiding tool 200 may include more than one clamp that is similar to clamp 204. For example, body 202 may include a second clamp that may be configured to attach to the lateral condyle of the femur 212 in addition to the clamp 204. The use of a second clamp may add further stability of the surgical guiding tool 200 to the femur 212.

The use of the first portion 214 along with one or more clamps, such as clamp 204, ensures that the surgical guiding tool remains secured to the femur 212, or other bone, even with limited attachment regions on the bones for attaching the guiding tool (e.g., due to cartilage regions not being visible on the images of CT scans, as described above). By securing the surgical guiding tool 200 in a stable manner using the first portion 214 and the one or more clamps, the surgical guiding tool may be securely and accurately placed on the bone so that surgery may be performed more accurately and safely due to little or no movement of the guide. For example, by attaching the first portion 214 to the anterior region of the femur 212 (e.g., to an osteophyte), and further attaching one or more clamps, such as clamp 204, to one or more condyles, the surgical guiding tool 200 will be restricted from various translational and rotational movements (e.g., posterior and anterior sliding, distal and proximal sliding, mediolateral sliding, internal-external rotation, varus-valgus movements, and/or flexion-extension).

Figure 1B:
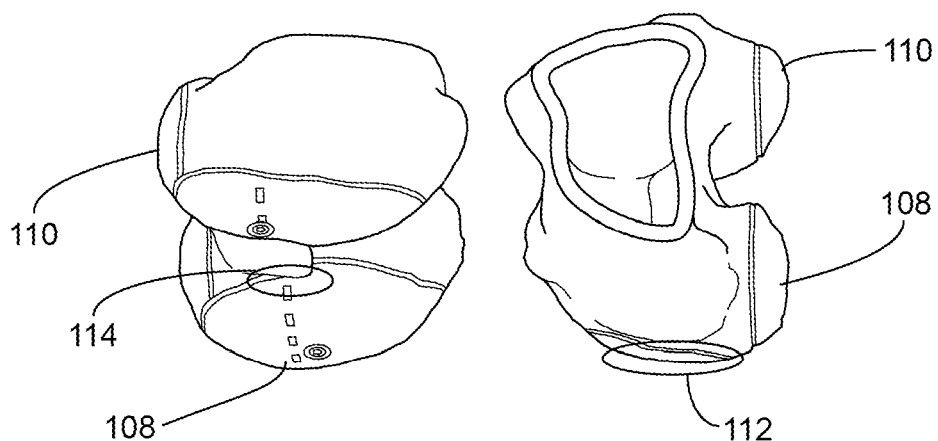

The surgical guiding tool 200 further includes apertures 206, 208, and 210, which may aligned with areas of the femur 212 corresponding to locations that need to be accessed for surgery, such as locations where holes are to be drilled. For example, holes 104 and 106 illustrated in FIG. 1 may be aligned with the apertures 206 and may be created using a surgical tool device inserted into the apertures 206, such as a drill, bur, saw, jig saw, lateral drill or any other cutting, milling or drilling instrument. The apertures 206, 208, and 210 are positioned so that a surgical tool device that is passed through one or more of the apertures 206, 208, and 210 can reach the bone at the desired location. The apertures 206, 208, and 210 may be positioned in any direction relative to the bone as long as it provides access for a surgical tool device to reach the bone at the desired location. In some embodiments, the apertures 206, 208, and 210 may protrude from the surface of the body 214, as illustrated in FIGS. 2*a* and 2*b*. In some embodiments, the apertures may include safety stops to prevent a surgical tool device from advancing beyond a planned or determined depth into the bone. While the description herein may describe apertures 206, 208, and 210 located at specific locations, one of skill in the art will understand that the content of the present application applies equally to aperture locations relating to patient-specific locations on different type of bones, and may be determined using pre-operative procedures described above. Further, the orientation and position of the apertures may correspond to pre-operative planning and procedures.

In some embodiments, the surgical guiding tool 200 may be a single, continuous structure (e.g., a single mold) that includes all of the guiding tool components, including the body 214, the apertures 206, 208, and 210, and the clamp 204. In some embodiments, the each component of the surgical guiding tool 200 may be a separate structure that is integrated with the other components to create the surgical guiding tool 200.

Figure 3:
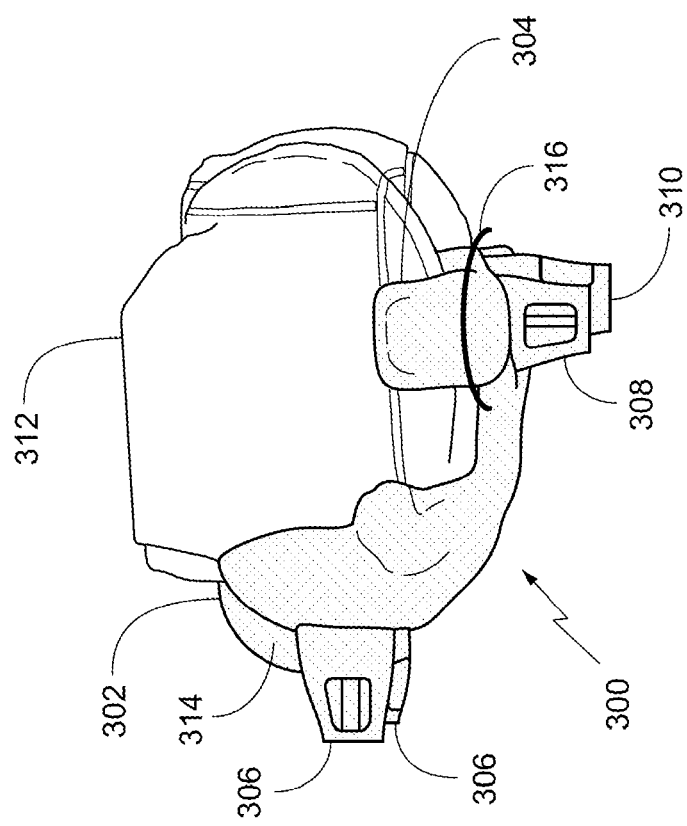
FIG. 3 illustrates another example of a surgical guiding tool configured to attach to a bone and including a flexible structure.

FIG. 3 illustrates another example of a surgical guiding tool 300 configured to attach to a bone and including a flexible structure 316. In some embodiments, the surgical guiding tool 300 may be a femoral surgical guiding tool for a distal end of a femur 312. While the description herein may describe a femur 312 as an example of the bone, one of skill in the art will understand that the content of the present application applies equally to other bones, such as the humerus, scapula, tibia, fibula, talus, and other shoulder, hip, ankle, and/or finger bones. Similar to the surgical guiding tool 200 illustrated in FIG. 2, surgical guiding tool 300 includes a body 302, a clamp 304, apertures 306, 308, and 310, and a first portion 314 (e.g., an anterior portion). The body 302 is configured to attach to at least one region or portion of the femur 312 and includes a first portion 314, such as an anterior portion, that is configured to attach the surgical guiding tool to an anterior region of the femur 312. For example, the first portion 314 may be configured to attach the surgical guiding tool 300 to one or more osteophytes on the anterior region of a femur 312. In some embodiments, the first portion 314 may be configured to attach the surgical guiding tool to one or more osteophytes anywhere along a bone, such as one or more osteophytes on the distal end of a humerus. In some embodiments, the first portion 314 may be configured to rest on one or more portions of the femur 312 (e.g., one or more osteophytes) and thus restrict undesired movement of the surgical guiding tool 300. In these embodiments, the clamp 304 may be used to secure the surgical guiding tool 300 to the femur 312. In some embodiments, the first portion 314 may include a flexible snap-fit portion for increasing a clamping force of the first portion 314 to the femur 312 and allowing ease of removal of the surgical guiding tool 300 from the femur 312. For example, the first portion 314 may be manufactured from a flexible material that creates a clamping force for squeezing a portion of a femur 312 (e.g., an osteophyte), and at the same time allows a physician to easily remove the surgical guiding tool 300 from the femur 312.

The clamp 304 is configured to attach the surgical guiding tool 300 to one or more portions of the femur 312, such as a medial condyle as illustrated in FIG. 3. The clamp 304 may include a snap-fit portion including flexible structure 316 for increasing a clamping force of the clamp 304 and allowing ease of removal of the surgical guiding tool 300 from the femur 313. The snap-fit portion may be configured to allow a stable and secure attachment of the surgical guiding tool 300 to a condyle of the femur 312 by increasing the clamping force of the clamp 304, while allowing a physician to remove the surgical guiding tool 300 from the femur 312 with ease. The flexible structure 316 of the snap-fit portion may include material having a thickness that is less than the average thickness of the remainder of the body 302. By manufacturing the flexible structure 316 of the snap-fit portion to be thinner than the remainder of the body, the desired flexibility of the clamp 304 of the guiding tool 300 may be obtained because the thinner portion introduces a weakened area in the clamp 304, which allows bending of the snap-fit portion of the clamp 304. For example, the flexible structure 406 provides flexibility so that a physician is able to easily manipulate the clamp 304 to fit around a condyle of the femur 312, and at the same time provides a clamping force sufficient to securely attach the surgical guiding tool 300 to the femur 312 in a stable and secure manner. In some embodiments, the flexible structure 316 may have a thickness that is between ½ and ⅕ of the average thickness of the remainder of the body 302. In some embodiments, the minimum thickness of the flexible structure is about 2 mm, to maintain stability of the structure. In some embodiments, the body 302 of the surgical guiding tool 300 may include more than one clamp that is similar to clamp 304. For example, body 302 may include a second clamp that may be configured to attach to the lateral condyle of the femur 312 in addition to the clamp 304. The use of a second clamp may add further stability of the surgical guiding tool 300 to the femur 212. In some embodiments, the body 302 may include a first clamp, such as clamp 304, that includes a snap-fit portion including a flexible structure, such as flexible structure 316, and a second, non-flexible clamp (e.g., with an undercut portion). In some embodiments, the body 302 may include two or more clamps that include a snap-fit portion including a flexible structure.

Apertures 306, 308, and 310 are similar to the apertures illustrated in FIG. 2, and may aligned with areas of the femur 312 that correspond to locations that need to be accessed for surgery, such as locations where holes are to be drilled. For example, drill holes 104 and 106 illustrated in FIG. 1 may be aligned with the apertures 306 and may be created using a surgical tool device inserted into the apertures 206, such as a drill, bur, saw, jig saw, lateral drill or any other cutting, milling or drilling instrument. In some embodiments, the apertures 306, 308, and 310 may protrude from the surface of the body 314, as illustrated in FIG. 3. While the description herein may describe apertures 306, 308, and 310 located at specific locations, one of skill in the art will understand that the content of the present application applies equally to aperture locations relating to patient-specific locations on different type of bones, and may be determined using pre-operative procedures described above.

Figure 5:
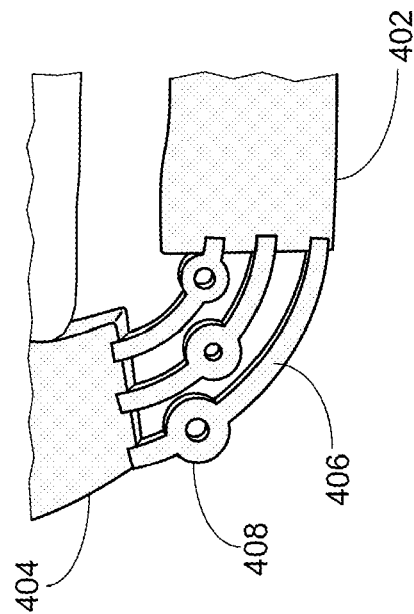
FIG. 5 illustrates an example of a flexible structure for use with a surgical guiding tool.
Figure 4:
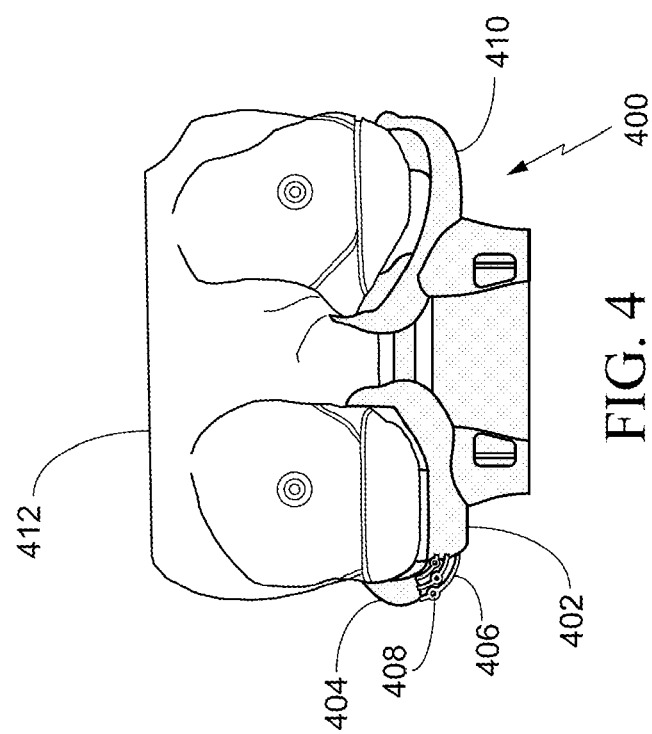
FIG. 4 illustrates yet another example of a surgical guiding tool configured to attach to a bone and including a flexible structure.

FIG. 4 illustrates yet another example of a surgical guiding tool 400 configured to attach to a bone, such as the femur 412, and including a flexible structure 406. The surgical guiding tool 400 includes a first clamp 402 and a second clamp 410. The first clamp 402 may include a snap-fit portion including flexible structure 406 for increasing a clamping force of the first clamp 402 and allowing ease of removal of the surgical guiding tool 400 from the femur 412. The snap-fit portion may be configured to allow a stable and secure attachment of the surgical guiding tool 400 to a condyle of the femur 412 by increasing the clamping force of the first clamp 402, while allowing a physician to remove the surgical guiding tool 400 from the femur 412 with ease. The flexible structure 406 includes one or more attachment mechanisms, such as a group of bands or chains, that interconnect a medial portion of the first clamp 402 to a lateral portion 404 of the first clamp 402. FIG. 5 illustrates an example of the flexible structure 406. The one or more attachment mechanisms of the flexible structure 406 provide the desired flexibility of the first clamp 402 of the surgical guiding tool 400 and allow bending of the snap-fit portion of the clamp 402. The one or more attachment mechanisms may include a group of bands or chains that are made from a flexible material (e.g., silicone, rubber, etc.) that provides a flexible attachment of the clamp 402 to the femur 412. For example, the one or more attachment mechanisms of the flexible structure 406 provides flexibility so that a physician can easily manipulate the clamp 402 to fit around the condyle of the femur 412, and at the same time provides a clamping force sufficient to securely attach the surgical guiding tool 400 to the femur 412 in a stable and secure manner. Each attachment mechanism of the flexible structure 406 may further include one or more cylinders 408 (e.g., one cylinder for each attachment mechanism) that add rigidity and stability to the flexible structure so that the clamp fits securely to the bone. Further, the one or more cylinders 408 may increase the clamping force for securely attaching the surgical guiding tool 400 to the femur 412.

Figure 6:
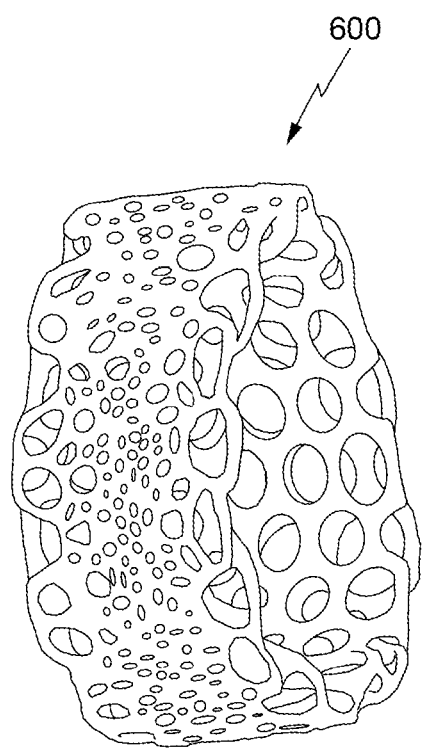
FIG. 6 illustrates another example of a flexible structure for use with a surgical guiding tool.

FIG. 6 illustrates another example of a flexible structure 600 for use with a surgical guiding tool, such as the surgical guiding tools described above. The flexible structure 600 includes a plurality of holes, and may be shaped like a honeycomb structure. The flexible structure 600 may be used in place of the one or more attachment mechanisms described above with respect to FIG. 5. For example, the flexible structure 600 may interconnect a medial portion of the first clamp 402 to a lateral portion 404 of the first clamp 402. The plurality of holes add flexibility so that a physician can easily manipulate a clamp using the flexible structure 600 to attach to a portion of a bone (e.g., a condyle of a femur). The plurality of holes further add rigidity for providing a clamping force sufficient to securely attach the surgical guiding tool 600 to the bone in a stable manner. The flexible structure 600 may be used to fit a clamp of a surgical guiding tool snugly around the condyle of a femur in order to provide a stable and secure fit of the surgical guiding tool to the femur.

One of skill in the art will understand that any flexible material may be used as the material for the attachment mechanism. In some embodiments, only materials that are biocompatible (e.g., USP class VI compatible) may be used as the attachment mechanism of the flexible structure 406.

In some embodiments, the second clamp 410 of the surgical guiding tool 400 may include an undercut portion when the surgical guiding tool 400 is placed on the femur 412. For example, an undercut portion of the second clamp 410 may form a clamping or snapping mechanism that encloses a condyle, such as the lateral condyle illustrated in FIG. 4, and creates a stable and secure attachment of the surgical guiding tool 400 to the femur 412.

In some embodiments, the second clamp 410 may include a snap-fit portion including flexible structure for increasing a clamping force of the clamp 410 and allowing ease of removal of the surgical guiding tool 400 from the femur 412. The flexible structure of the snap-fit portion may include material having a thickness that is less than the average thickness of the remainder of the body of the surgical guiding tool 400, or may include one or more attachment mechanisms similar to the flexible structure 406 of the first clamp 402.

In some embodiments, the surgical guiding tools 200, 300, and/or 400 may be a single, continuous structure (e.g., a single mold) that includes all of the guiding tool components, including the body, the apertures, and the one or more clamps. In some embodiments, the each component of the surgical guiding tools 200, 300, and/or 400 may be a separate structure that is integrated with the other components to create the surgical guiding tools.

FIG. 7a illustrates a clamping structure 700 that may act as a retractor. The clamping structure 700 includes a body 702 and a clamp 704. The clamp 704 includes an engagement surface 706 that may anatomically match part of a bone of a patient, such as a knee, shoulder, ankle, etc. In some embodiments, the clamping structure 700 includes a coupling feature 708 that allows a removable coupling of the body 702 and the clamp 704 to one another. For example, the coupling feature 708 may form a dovetail coupling. The body 702 further includes a clipping portion 710 (e.g., a rotation clip).

FIGS. 7b illustrates an embodiment including the clamping structure 700 used with a surgical guiding tool 712 (eg., a patient specific surgical guiding tool). For example, the surgical guiding tool 712 may be used for positioning on a shoulder bone 714. While the description herein may describe a shoulder bone 714 as an example of the bone, one of skill in the art will understand that the content of the present application applies equally to other bones, such as the femur, humerus, scapula, tibia, fibula, talus, and other shoulder, hip, ankle, and/or finger bones. The surgical guiding tool may be used to guide the drilling of a hole in the bone 714 via a drill guide 716. The clamping structure 700 may begin in a position suitable for insertion or removal of the clamping structure into the patient. The clipping portion 710 fits onto a corresponding portion of the surgical guiding tool 712. The clamp 704 of the clamping structure 700 comprises a retractor surface that matches the anatomy of the shoulder bone over which it will be applying force when the retractor surface of the clamping structure is in its engaged position. In FIG. 7b, the clamping structure 700 is illustrated in an engaged position. In this position, the retractor surface of the clamping structure is engaged to the surgical guiding tool 712 and pulls the guide towards the bone surface, thereby creating a clamp and thus producing a secure and stable locking fit. The clamping structure 700 further operates to pull back the skin of the patient while providing the clamping force to the bone.

In some embodiments, the clamping structure 700 may be integrated with a surgical guiding tool, such as guiding tools 200, 300, 400, and/or 716, so that the surgical guiding tool includes a single structure including the clamping structure 700. Integration of the clamping structure 700 with the surgical guiding tool allows a ratcheting clamping structure for providing a secure and stable placement of the surgical guiding tool to a bone. In some embodiments, a surgical guiding tool may include two clamping structures 700 on two opposite sides of the surgical guiding tool. Providing two clamping structures 700 allows a ratcheting force on two sides of the surgical guiding too, providing an even more stable and secure clamping force.

In some embodiments, the clamping structure 700 used as a retractor may include any structure for locking clamping structure 700 into place so that a physician may operate without holding the retractor in place. For example, the clamping structure 700 may include a ratchet retractor that may be used to lock the clamping structure 700 in place. The ratchet retractor may have multiple locking positions that allow a variable opening in the surgical location of the patient.

In some embodiments, the retractor may be provided with holes or other features that allow the placing of pins into the bone 714, thereby locking the surgical guiding tool and retractor into place. In some embodiments, the surgical guiding tool 712 may further include a coupling feature that allows integration of a surgical instrument into the surgical guiding tool. The coupling feature may have a shape that matches the shape of (a part of) the surgical instrument.

Figure 8A:
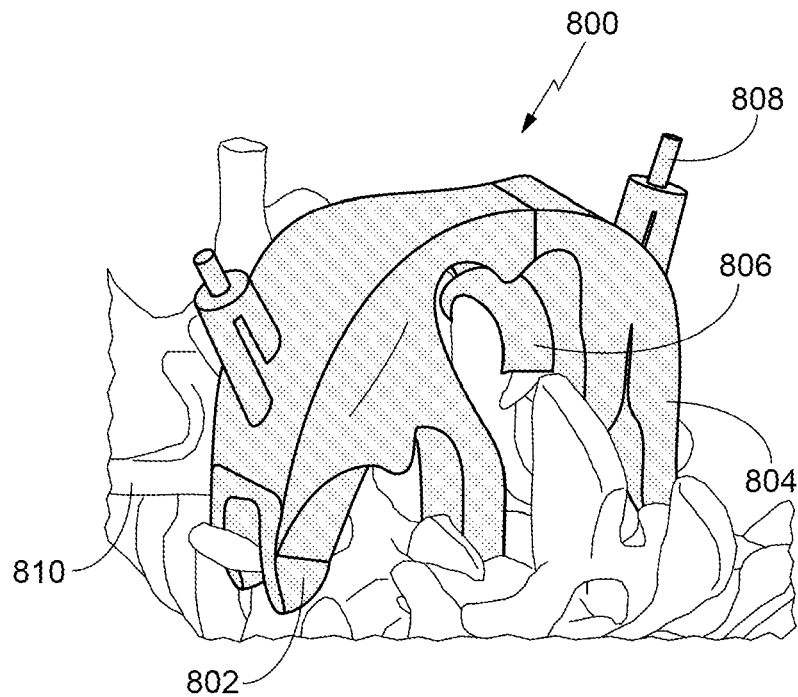
FIGS. 8a and 8b illustrates an example of a surgical guiding tool configured to attach to a spine.
Figure 8B:
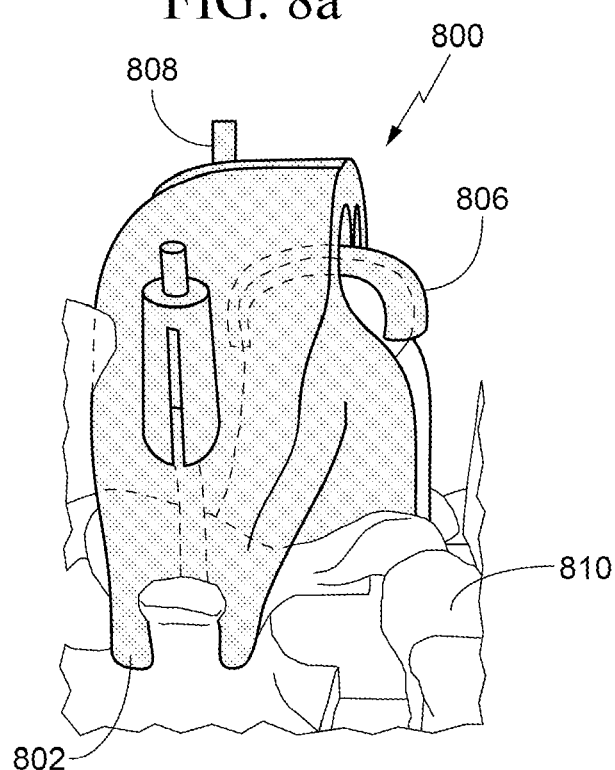

FIGS. 8a and 8b illustrate an example of a surgical guiding tool 800 configured to attach to a spine 810. The surgical guiding tool 800 includes a first transverse process clamp 802, a second transverse process clamp 804, a spinous process clamp 806, and a guiding element 808. The first and second transverse process clamps 802 and 804 include clamps that are able to provide a secure and stable attachment to the transverse process portions of the spine 810. The spinous process clamp 806 further provides a secure attachment to the spinous process of the spine 810. Any of the clamps described above with respect to FIGS. 2-7 may be used for the first and second transverse process clamps 802 and 804 and/or the spinous process clamp 806. For example, an overhang of the ends (i.e., an undercut portion) of the clamps 802, 804, and/or 806 may be created when the surgical guiding tool 800 is placed on the spine 810. The undercut portion may form a clamping or snapping mechanism that encloses the transverse process and creates a stable and secure attachment of the surgical guiding tool 800 to the spine 810. As another example, the clamps 802, 804, and 806 may include a snap-fit portion including a flexible structure for increasing a clamping force of the clamps 802, 804, and 806 and allowing ease of removal of the surgical guiding tool 800 from the spine 810. In some embodiments, the flexible snap-fit portion including the flexible structure may include material having a thickness that is less than the average thickness of the remainder of the guide 800, as described above. In some embodiments, the flexible snap-fit portion including the flexible structure may include one or more attachment mechanisms, as described above, that may include a group of bands, chains, or a honeycomb structure that are made from a flexible material. The surgical guiding tool may further include a guiding element 808. The guiding element 808 may include an aperture through which a surgical instrument may be placed. The guiding element 808 may further include a drill pin, or any other tool used in a surgical procedure relating to the spine. For example, a drill pin may be used to lock the guide 800 into place on the spine 810. In some embodiments, any number of clamps may be used to attach the surgical guiding tool 800 to the spine 810. For example, a clamp may further be used to attach the surgical guiding tool 800 to the lamina, the superior process articular, the pedicle, etc.

In some embodiments, the surgical guiding tools 200, 300, 400, 716, and/or 800 illustrated in FIGS. 2-4, 7, and 8 may include one or more handle structures (not shown) that protrude from the outer surface of the surgical guiding tool. The one or more handle structures may be used to allow easy manipulation of the guiding tools, such as for handling the guiding tools. For example, the one or more handles may be used for placing the guiding tools over the bone or removing them from the bone. In some embodiments, the handle structures may function to open a clamp, such as clamp 204, 304, 402, 704, 802, 804, and/or 806, of the guiding tool by forcing two or more of the handle structures together. Thus, the one or more handles may allow easier placement or removal of the guiding tool over or from the bone.

Figure 9:
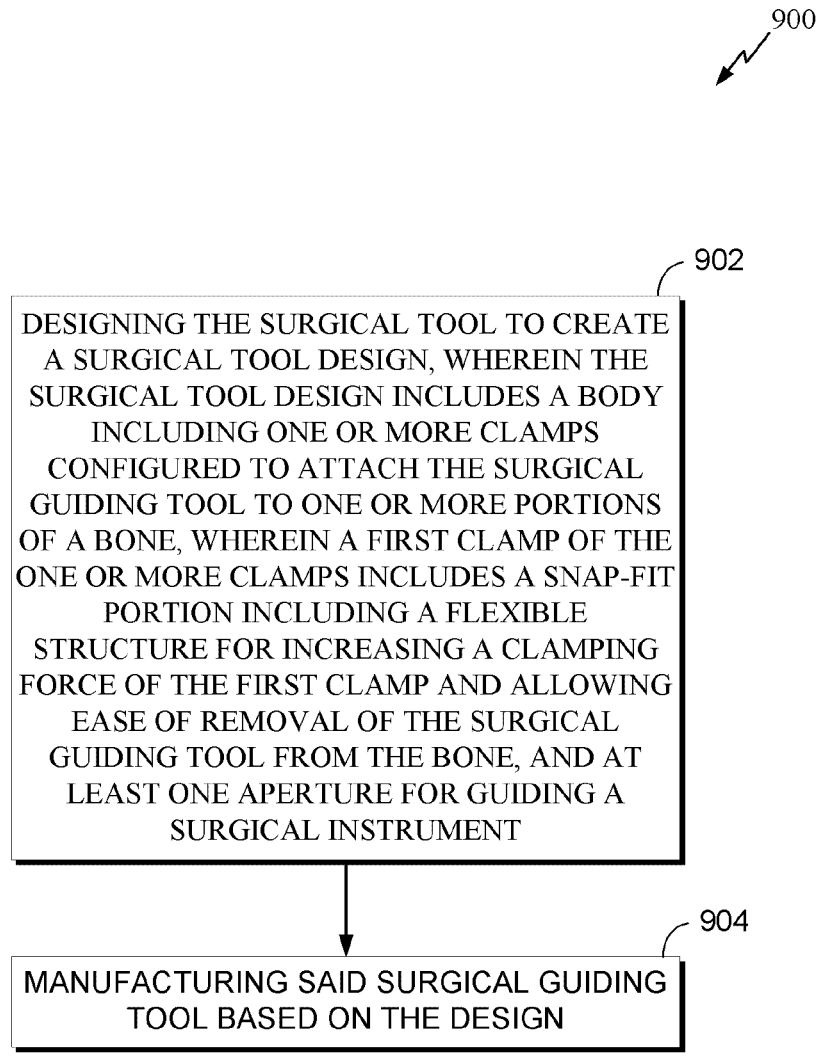
FIG. 9 illustrates an aspect of a method of manufacturing a surgical guiding tool.

FIG. 9 illustrates a method of manufacturing a surgical guiding tool. At block 902, the method includes designing the surgical guiding tool to create a surgical tool design, wherein the surgical guiding tool design includes: a body including one or more clamps configured to attach the surgical guiding tool to one or more portions of a bone, wherein a first clamp of the one or more clamps includes a snap-fit portion including a flexible structure for increasing a clamping force of the first clamp and allowing ease of removal of the surgical guiding tool from the bone, and at least one aperture for guiding a surgical instrument. At block 904, the method includes manufacturing the surgical guiding tool based on the surgical guiding tool design. The surgical guiding tool may be designed and/or manufactured according to the pre-operative planning procedures using patient-specific features of a patient's bone discussed above. In some embodiments, the snap-fit portion is manufactured to provide a level of force specified in the design.

In some embodiments, the surgical guiding tools described above are partially or completely made by additive manufacturing, which allows the integration of patient-specific components (e.g., the body, the one or more clamps, the apertures, etc.) that further increases the accuracy of the guiding tools. The patient-specific components of the surgical guiding tools may be designed based on patient-specific parts of a particular bone of a patient. The patient specific components of the surgical guiding tools may be made by generating portions that are complementary to the patient-specific parts of the bone. For converting digital image information of the bone into a basic model, template, or mold that at least in part shows the positive or negative form of at least a portion of the bone, any suitable technique known in the art may be used, such as for example a rapid prototyping technique.

Rapid Prototyping and Manufacturing (RP&M) may be defined as a group of techniques used to quickly fabricate a scale model of an object typically using three-dimensional (3-D) computer aided design (CAD) data of the object. Currently, a multitude of Rapid Prototyping techniques are available, including stereo lithography (SLA), Selective Laser Sintering (SLS), Fused Deposition Modeling (FDM), foil-based techniques, etc.

A common feature of these techniques is that objects are typically built layer by layer. Stereo lithography, presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described, for example, in U.S. Pat. No. 5,141,680, the entire disclosure of which is hereby incorporated by reference.

Foil-based techniques fix coats to one another by means of gluing or photo polymerization or other techniques and cut the object from these coats or polymerize the object.

Typically RP&M techniques start from a digital representation of the 3-D object to be formed. Generally, the digital is sliced into a series of cross-sectional layers which can be overlaid to form the object as a whole. The RP&M apparatus uses this data for building the object on a layer-by-layer basic. The cross-sectional data representing the layer data of the 3-D object may be generated using a computer system and computer aided design and manufacturing (CAD/CAM) software.

A selective laser sintering (SLS) apparatus may be used for the manufacture of a surgical guiding tool template instead of a computer model. It should be understood however, that various types of rapid manufacturing and tooling may be used for accurately fabricating these surgical templates including, but not limited to, stereolithography (SLA), Fused Deposition Modeling (FDM) or milling.

The surgical guiding tools described above (or parts thereof) may be manufactured using different materials. In some embodiments, only materials that are biocompatible (e.g. USP class VI compatible) with the human body are used. In some embodiments, a surgical guiding tool template may be formed from a heat-tolerable material allowing it to tolerate high-temperature sterilization. In some embodiments, if SLS is used as a RP&M technique, the surgical guiding tool template may be fabricated from a polyamide such as PA 2200 as supplied by EOS, Munich, Germany or any other material known by those skilled in the art may also be used.

The invention disclosed herein may be implemented as a method, apparatus, or article of manufacture using standard programming or engineering techniques to produce software, firmware, hardware, or any combination thereof. The term "article of manufacture" as used herein refers to code or logic implemented in hardware or nontransitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

It will be appreciated by persons skilled in the art that numerous variations and/or modifications may be made to the invention without departing from the spirit or the scope of the invention as broadly described. The above described embodiments are, therefore, to be considered in all respects as illustrative and not restrictive.

What is claimed is:

1. A surgical guiding tool for a bone comprising:
a body including:
one or more clamps configured to attach the surgical guiding tool to one or more portions of the bone and restrict movement, wherein a first clamp of the one or more clamps includes a snap-fit portion including a flexible structure for increasing a clamping force of the first clamp and allowing ease of removal of the surgical guiding tool, wherein the flexible structure of the snap-fit portion includes a honeycomb structure including a plurality of holes that add flexibility and rigidity to the flexible structure;
a first portion configured to attach the surgical guiding tool to an osteophyte on the bone to restrict movement; and
at least one aperture for guiding a surgical instrument.

2. The surgical guiding tool of claim 1, wherein the first portion is configured to create a clamping force for squeezing the osteophyte on the bone to restrict the movement.

3. The surgical guiding tool of claim 1, wherein the flexible structure of the snap-fit portion includes material having a thickness that is between ½ and ⅕ of the average thickness of the remainder of the body.

4. The surgical guiding tool of claim 1, wherein the first clamp comprises an undercut portion.

5. The surgical guiding tool of claim 4, wherein the undercut portion forms a clamping mechanism that is configured to enclose a condyle of the bone.

6. The surgical guiding tool of claim 1, wherein the bone is one of a shoulder or a femur.

7. The surgical guiding tool of claim 1, wherein the first portion includes another flexible snap-fit portion for increasing a clamping force of the first portion to the osteophyte and allowing ease of removal of the surgical guiding tool from the osteophyte.

8. The surgical guiding tool of claim 1, wherein the bone is a femur and the one or more portions of the bone that the one or more clamps are configured to attach the surgical guiding tool to include at least one condyle of the distal end of the femur.

9. The surgical guiding tool of claim 1, wherein the flexible structure includes a flexible material.

10. A surgical guiding tool for a bone comprising:
a body including:
one or more clamps configured to attach the surgical guiding tool to one or more portions of the bone and restrict movement, wherein a first clamp of the one or more clamps includes a snap-fit portion including a flexible structure for increasing a clamping force of the first clamp and allowing ease of removal of the surgical guiding tool, wherein the flexible structure of the snap-fit portion includes at least one chain connected between a first portion of the first clamp and a second portion of the first clamp, wherein the at least one chain includes at least one cylinder adding rigidity to the at least one chain;
a first portion configured to attach the surgical guiding tool to an osteophyte on the bone to restrict movement; and
at least one aperture for guiding a surgical instrument.

11. The surgical guiding tool of claim 10, wherein the first portion is configured to create a clamping force for squeezing the osteophyte on the bone to restrict the movement.

12. The surgical guiding tool of claim 10, wherein the flexible structure of the snap-fit portion includes material having a thickness that is between ½ and ⅕ of the average thickness of the remainder of the body.

13. The surgical guiding tool of claim 10, wherein the first clamp comprises an undercut portion.

14. The surgical guiding tool of claim 13, wherein the undercut portion forms a clamping mechanism that is configured to enclose a condyle of the bone.

15. The surgical guiding tool of claim 10, wherein the bone is one of a shoulder or a femur.

16. The surgical guiding tool of claim 10, wherein the first portion includes another flexible snap-fit portion for increasing a clamping force of the first portion to the osteophyte and allowing ease of removal of the surgical guiding tool from the osteophyte.

17. The surgical guiding tool of claim 10, wherein the bone is a femur and the one or more portions of the bone that the one or more clamps are configured to attach the surgical guiding tool to include at least one condyle of the distal end of the femur.

18. The surgical guiding tool of claim 10, wherein the flexible structure includes a flexible material.

* * * * *